United States Patent [19]

Kurosu et al.

[11] 4,281,016
[45] Jul. 28, 1981

[54] NEMATOCIDAL COMPOSITION

[75] Inventors: Yasuhisa Kurosu, Fujimi; Hiroshi Kawada, Tokyo; Haruki Kanasugi, Tokyo; Akiko Kashima, Tokyo, all of Japan

[73] Assignee: Hodogaya Chemicals Co., Ltd., Tokyo, Japan

[21] Appl. No.: 53,550

[22] Filed: Jun. 29, 1979

[30] Foreign Application Priority Data

Jul. 18, 1978 [JP] Japan ................................ 53-86706
Feb. 24, 1979 [JP] Japan ................................ 54-20233

[51] Int. Cl.$^3$ ..................... A01N 47/10; C07C 155/08
[52] U.S. Cl. ................................. 424/300; 260/455 A
[58] Field of Search ..................... 260/455 A; 424/300

[56] References Cited

U.S. PATENT DOCUMENTS 2,847,419  8/1958  Harrman ..................... 260/455 A
2,943,972  7/1960  van der Kerk ................. 260/455 A

OTHER PUBLICATIONS

Chem. Abstracts, vol. 71, 1969, 38294c.
Chem. Abstracts, vol. 69, 1968, 77268a.

Primary Examiner—John M. Ford
Assistant Examiner—Robert C. Whittenbaugh
Attorney, Agent, or Firm—Cushman, Darby & Cushman

[57] ABSTRACT

A nematocidal composition containing as active ingredient(s) dithiocarbamate compound(s) represented by the general formula,

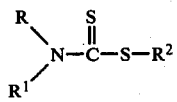

wherein R and R$^1$ are each lower alkyl groups and R$^2$ is a group of —CH$_2$C≡CH, —CH$_2$CH=CH$_2$,

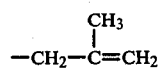

or —CH$_2$—CH=CHCH$_3$.

8 Claims, No Drawings

NEMATOCIDAL COMPOSITION

This invention relates to a nematocidal composition containing a dithiocarbamate compound as the active ingredient.

In the countries where upland farming is the mainstay of agriculture, damages of the annual or perennial plants by the injurious soil nematodes such as root-knot nematodes, root-lesion nematodes and cyst nematodes are a large problem, and they are laboring to find out a method of control for such injurious soil nematodes. Development of a safe and effective nematocidal compositions is thus keenly requested.

Heretofore, a number of different kinds of nematocides have been developed and practically used for controlling of said injurious soil nematodes. In use, most of these nematocides are diffused into the soil in the form of a gas to kill the nematodes which come into contact with the diffused gas. Among of them, typical compounds used for such nematocides are, for example, EDB (1,2-dibromoethane), D-D (1,3-dichloropropene and 1,2-dichloropropane), chloropicrin (trichloronitromethane), methyl bromide, carbam (ammonium or sodium N-methyl-dithiocarbamate), DCIP (bis-[2-chloro-1-methylethyl]ether) and DBCP (1,2-dibromo-3-chloropropane). These compounds can be gasified at a normal temperature and easily diffused into the soil, so that they produce a relatively high killing effect against the injurious soil pests. On the other hand, because of their strong toxicity, inflammability and irritative action, their use in the neighborhood of cities is attended by many problems, and certain restrictions are imposed on their storage and use. Also, damage to crops from these chemicals is not a few and no planting is allowed unless the gaseous compounds diffused in the soil are eliminated. Further, because of their non-specific killing effect against the living things in the soil, these compounds might annihilate even the useful organisms living in the soil, and if the injurious soil nematodes are given a chance to again invade to the once treated soil, the density of such nematodes will increase in such soil rapidly, and on the second year after planting, even a greater degree of damage may be caused than in the non-treated soil.

The present inventors have made further studies on the compounds effective for controlling the injurious soil nematodes and found that certain dithiocarbamate compounds have a specific killing effect against such nematodes. This invention was completed on the basis of such findings.

There are known many dithiocarbamate compounds which are useful as herbicides or fungicides, and the above-mentioned carbam compounds are already commercialized as nematocides. The carbam compounds are strongly irritative to the skin, and it is considered that they are decomposed in the soil into a methyl isothiocyanate gas to produce a nematocidal effect. The compounds provided according to this invention are N,N-dialkyldithiocarbamates which, like said carbam compounds, are different from N-monoalkyldithiocarbamates in decomposing properties and made of action.

The dithiocarbamate derivatives according to this invention can be easily obtained by reacting dialkylamine with carbon disulfide and further reacting the resultant product with an allyl halide, a methylallyl halide, a propargyl halide or a crotyl halide.

Shown below are the processes for the synthesis of some typical compounds provided according to this invention.

SYNTHESIS EXAMPLE 1

Synthesis of propargyl-N,N-dimethyldithiocarbamate 16.3 Grams of a 40% dimethylamine aqueous solution was added to 40 ml of dimethylformamide, and while maintaining the mixture at a temperature of 5°–10° C., 4.8 gr of carbon disulfide was added dropwise under agitation over the period of 30 minutes. Thereafter, the temperature of the mixture was maintained at a room temperature and 7.1 gr of propargyl bromide was added dropwise thereto over the period of 30 minutes. The reaction mixture was agitated at the same temperature for one hour and at 40°–50° C. for additional two hours to complete the reaction. The reaction mixture was poured into water and the separated organic substance was extracted twice with 50 ml of benzene, washed with diluted hydrochloric acid and further washed with water, and after removal of benzene by distillation, 9.2 gr of the desired product was obtained. M.p.: 57°–59° C. The results of elemental analysis were shown as follows:

|  | C | H | N | S |
|---|---|---|---|---|
| Calculated (%): | 45.28 | 5.66 | 8.81 | 40.25 |
| Found (%): | 45.33 | 5.68 | 8.76 | 39.91 |

SYNTHESIS EXAMPLE 2

Synthesis of allyl-N,N-dimethyldithiocarbamate

The same procedures of reaction and treatment as practiced in Synthesis Example 1 were repeated except that by using 7.3 gr of allyl bromide instead of propargyl bromide to obtain 9.0 gr of the desired product which is oily at a room temperature. B.p.: 119° C./8 mmHg.

Refractive index: $n_D^{20}$ 1.6042.

Elemental analysis:

|  | C | H | N | S |
|---|---|---|---|---|
| Calculated (%): | 44.72 | 6.82 | 8.70 | 39.75 |
| Found (%): | 44.75 | 6.87 | 8.71 | 39.80 |

SYNTHESIS EXAMPLE 3

Synthesis of 2-methylallyl-N,N-dimethyldithiocarbamate

The process of Synthesis Example 1 was repeated except that by using 5.5 gr of 2-methylallyl chloride instead of propargyl bromide to obtain 8.1 gr of the desired product which is oily at a room temperature.

Refractive index: $n_D^{20}$ 1.5745.

Elemental analysis:

|  | C | H | N | S |
|---|---|---|---|---|
| Calculated (%): | 48.00 | 7.43 | 8.00 | 36.57 |
| Found (%): | 48.11 | 7.50 | 8.12 | 36.30 |

SYNTHESIS EXAMPLE 4

Synthesis of crotyl-N,N-dimethyldithiocarbamate 12.0 Grams of a 50% dimethylamine aqueous solution was added to 30 ml of tetrahydrofuran, and to this mixture being maintained a temperature at 0°–5° C., was added dropwise 5.0 gr of carbon disulfide under agitation over the period of 30 minutes. Thereafter, the reaction mixture was maintained at a room temperature and further 5.4 gr of crotyl chloride was added dropwise thereto over the period of 30 minutes, and this was followed by 3-hour agitation at the same temperature to complete the reaction. The reaction mixture was poured into water and the separated organic substance was extracted twice with 30 ml of toluene, washed with diluted hydrochloric acid and further washed with water, and then toluene was removed by distillation to obtain 10.2 gr of the desired product having the following physical properties.

Refractive index: $n_D^{20}$ 1.5880
Elemental analysis:

|  | C | H | N | S |
|---|---|---|---|---|
| Calculated (%): | 48.00 | 7.43 | 8.01 | 36.57 |
| Found (%): | 48.00 | 7.67 | 7.98 | 36.48 |

SYNTHESIS EXAMPLE 5

Synthesis of allyl-N,N-diethyldithiocarbamate 9.7 Grams of diethylamine was added to 50 ml of tetrahydrofuran, and while maintaining the mixture at a temperature of 0°–5° C. and under agitation, 5.0 gr of carbon disulfide was added dropwise to the mixture over the period of 30 minutes. Thereafter, the temperature of the mixture was allowed to rise up to a room temperature, followed by dropwise addition of 4.6 gr of allyl chloride over the period of 30 minutes. The reaction mixture was poured into water and the separated organic substance was extracted twice with 30 ml of toluene, washed with diluted hydrochloric acid and further washed with water. After removal of toluene by distillation, there was obtained 8.3 gr of the desired product.

Refractive index: $n_D^{20}$ 1.5755
Elemental analysis:

|  | C | H | N | S |
|---|---|---|---|---|
| Calculated (%): | 50.79 | 7.94 | 7.40 | 33.86 |
| Found (%): | 50.85 | 8.00 | 7.39 | 33.78 |

SYNTHESIS EXAMPLE 6

Synthesis of allyl-N,N-dipropyldithiocarbamate 13.4 Grams of dipropylamine was added to 50 ml of tetrahydrofuran, and to this mixture being maintained a temperature at 0°–5° C., was added dropwise 5.0 gr of carbon disulfide over the period of 30 minutes under agitation. Thereafter, the mixture was maintained at a room temperature and 7.3 gr of allyl bromide was added dropwise thereto over the period of 30 minutes. The mixture was agitated at the same temperature for 3 hours to complete the reaction. The reaction mixture was poured into water and the separated organic substance was extracted twice with 30 ml of toluene and washed with diluted hydrochloric acid, followed by further washing with water. After removal of toluene by distillation to obtain 9.7 gr of the desired product.

Refractive index: $n_D^{20}$ 1.5525
Elemental analysis:

|  | C | H | N | S |
|---|---|---|---|---|
| Calculated (%): | 55.30 | 8.76 | 6.45 | 29.49 |
| Found (%): | 55.27 | 8.81 | 6.51 | 29.51 |

The compounds according to this invention may be mixed with various types of carriers to prepare them into a desired form of use such as emulsifiable concentrate, wettable powder, granules, dust, etc. The carriers used for such preparations may be either liquid or solid form or may be a combination thereof. These carriers are inert organic solvents, and examples of solid carriers include bentonite, talc, kaoline-clay, diatomaceous earth and the like. Examples of liquid carriers include xylene, methylnaphthalene, isophorone, cyclohexanone and the like.

In manufacturing of various forms of preparations, the composition may also be blended with surface active agents and other additives for giving emulsifiability, dispersability, spreadability and other required properties. Any desired preparations can easily be obtained by utilizing the commonly employed techiques for agricultural chemicals preparations.

Also, the compounds according to this invention may be used not only independently but also in admixture with other agricultural chemicals such as herbicides, fungicides, insecticides, etc.

The present invention is described further in detail hereinbelow by way of embodiments thereof. All the "parts" appearing in the following descriptions are by weight.

EXAMPLE 1

Emulsifiable concentrate

The following materials were mixed and dissolved to prepare an emulsifiable concentrate.

| Allyl-N,N-dimethyldithiocarbamate | 50 parts |
|---|---|
| Xylene | 30 parts |
| Kawakazole (tradename for an emulsifier manufactured by Kawasakikasei Chemicals Ltd.) | 10 parts |
| Agrizole (tradename for an emulsifier manufactured by Kao Atras Co., Ltd.) | 10 parts |

EXAMPLE 2

Wettable powder

The following materials were mixed to prepare a wettable powder.

| 2-Methylallyl-N,N-dimethyldithiocarbamate | 50 parts |
|---|---|
| Carplex (tradename for a silica manufactured by Shionogi & Co., Ltd.) | 25 parts |
| Kaolin-clay | 20 parts |
| Solpol 5039 (tradename for a dispersant manufactured by Toho Chemicals Co., Ltd.) | 5 parts |

EXAMPLE 3

Dust

The following materials were mixed to prepare a dust.

| | |
|---|---|
| Propargyl-N,N-dimethyldithiocarbamate | 3 parts |
| Carplex | 5 parts |
| Fubasami-clay (air-elutriated clay manufactured by Onuki Mining Co., Ltd.) | 92 parts |

EXAMPLE 4

Granules

The following materials were mixed and prepared into granules according to an ordinary granulating method.

| | |
|---|---|
| Allyl-N,N-dimethyldithiocarbamate | 5 parts |
| Kaolin-clay | 55 parts |
| Bentonite | 30 parts |
| Sodium Lignin sulfonate | 5 parts |
| Carplex | 5 parts |

EXAMPLE 5

Granules

The following materials were mixed and prepared into granules according to an ordinary granulating method.

| | |
|---|---|
| Allyl-N,N-dimethyldithiocarbamate | 25 parts |
| Diatomaceous earth | 73.5 parts |
| Saffinol TGE (tradename for a surface active agent manufactured by Sankyo Kasei Co., Ltd.) | 1.5 parts |

EXAMPLE 6

Emulsifiable concentrate

The following materials were mixed and dissolved to prepare an emulsifiable concentrate.

| | |
|---|---|
| Allyl-N,N-diethyldithiocarbamate | 50 parts |
| Xylene | 30 parts |
| Kawakazole | 10 parts |
| Agrizole P-145 (tradename for an emulsifier manufactured by Kao Atras Co., Ltd.) | 10 parts |

EXAMPLE 7

Wettable powder

The following materials were mixed to prepare a wettable powder.

| | |
|---|---|
| Allyl-N,N-dipropyldithiocarbamate | 50 parts |
| Carplex | 25 parts |
| Kaolin-clay | 20 parts |
| Solpol 5039 | 5 parts |

EXAMPLE 8

Dust

The following materials were mixed and pulverized to prepare a dust.

| | |
|---|---|
| Crotyl-N,N-dimethyldithiocarbamate | 3 Parts |
| Carplex | 5 Parts |
| Fubasami-clay | 92 Parts |

EXAMPLE 9

Granules

The following materials were mixed and prepared into granules according to a common granulating method.

| | |
|---|---|
| Allyl-N,N-diethyldithiocarbamate | 25 parts |
| Kaolin-clay | 25 parts |
| Bentonite | 40 parts |
| Carplex | 5 parts |
| Sodium lignin sulfonate | 5 parts |

EXAMPLE 10

Granules

The following materials were mixed and prepared into granules according to a usual granulating method.

| | |
|---|---|
| Allyl-N,N-diethyldithiocarbamate | 25 parts |
| Kaolin-clay | 25 parts |
| Bentonite | 35 parts |
| Carplex | 10 parts |
| Rapisol B-80 (tradename for a dispersant manufactured by Nippon Oils and Fats Co., Ltd.) | 5 parts |

Now, the prominent nematode-killing effects of the compounds according to this invention are described by way of the test examples.

TEST EXAMPLE 1

Nematocidal activity on *Pratylenchus penetrans* and *Bursaphelenchus lignicolus*

The nematodes to be tested were the groups of individuals, mostly larvae, of two species of nematodes (*Pratylenchus penetrans* and *Bursaphelenchus lignicolus*) under indoor cultivation.

Each compound to be tested was dissolved in ethanol to 1% concentration, and this solution was diluted with a 0.1% aqueous solution of Tween 80 (tradename for polyoxyethylene sorbitan monooleate manufactured by Kao Atras Co., Ltd.) to a desired concentration. 10 Milliliter of each diluted solution was pipetted into a syracuse watch glass and said species of nematodes were placed therein (150 to 200 of nematodes per glass) and bred at 27° C. for 48 hours. Death and survival of the nematodes were examined under a binocular microscope to determine the mortality (%). The test was repeated four times. The results are shown in Table 1.

TABLE 1

| Compound Concentration (ppm) | Mortality (%) | | | | | | |
|---|---|---|---|---|---|---|---|
| | Pratylenchus penetrans | | | | Bursaphelenchus lignicolus | | |
| | 100 | 50 | 10 | 1 | 50 | 10 | 1 |
| Allyl-N,N-dimethyl-dithiocarbamate | 100 | 85.0 | 46.8 | 18.6 | 100 | 76.8 | 27.5 |
| 2-Methyl-allyl-N,N-dimethyl-dithiocarbamate | 100 | 91.3 | 56.2 | 25.0 | 100 | 87.5 | 30.1 |
| Propargyl-N,N-dimethyl-dithiocarbamate | 100 | 88.3 | 49.5 | 15.3 | 100 | 80.0 | 29.4 |
| (Control) DBCP | 100 | 75.1 | 36.3 | 1.2 | 92.4 | 65.5 | 4.8 |

TEXT EXAMPLE 2

Effectiveness on *Meloidogyne incognita* with tomatoes used as indicator

The soil in which *Meloidogyne incognita* nematodes were bred by using sweet potato as host plant was packed into an unglazed pots (5.5 cm in diameter and 5.5 cm in height), 50 gr of soil per pot, and a measured amount of a wettable powder prepared according to Example 2 was diluted with water and poured on the surface of each pot. After allowing the pots to stand for 24 hours, tomato seeds were sown in the pots (10 seeds of tomato per pot). As for the carbam compound tested, a measured amount of this compound (in liquid state) was absorbed into a piece of cotton and the cotton was placed in a 5 cm deep hole bored in the center of each pot and covered with soil. Tomato seeds were sown (10 seeds per pot) on the 10th day after the treatment. The test was carried out in a glass hothouse (at a temperature of 25°–30° C.), and one month after the treatment, the rate of parasitic knots and phytotoxicity were examined. The rate of parasitic knots and the degree of phytotoxicity were expressed by the following rating. The results were as shown in Table 2 below. The test was repeated three times.

TABLE 2

| Rate of parasitic knots: | 0 | None |
|---|---|---|
| | 1 | Light |
| | 2 | Moderate |
| | 3 | Heavy |
| | 4 | Severe |
| Rate of phytotoxicity: | − | No sign of chemical damage |
| | ± | Growth was slightly affected and leaf blades were discolored. |
| | + | Growth was bad and leaf blades were discolored |
| | ++ | Growth was very bad and all leaves were browned |
| | +++ | Almost blasted |

| Compound | Dosage (kg/10a) | Rate of parasitic knots | Rate of phyto-toxicity |
|---|---|---|---|
| Allyl-N,N-dimethyldithio-carbamate | 10 | 0 | ± |
| | 5 | 0 | − |
| 50% wettable powder | 2.5 | 1.5 | − |
| 2-Methylallyl-N,N-dimethyl-dithiocarbamate | 10 | 0 | ± |
| | 5 | 0 | − |

TABLE 2-continued

| 50% wettable power | 2.5 | 1.2 | − |
|---|---|---|---|
| Propargyl-N,N-dimethyl-dithiocarbamate | 10 | 0 | ± |
| | 5 | 0.5 | − |
| 50% wettable power | 2.5 | 1.2 | − |
| (Control) | 10 | 0 | + |
| Carbam | 5 | 0.6 | ± |
| 50% liquid | 2.5 | 2.5 | − |
| Non-treated | − | 4 | − |

TEST EXAMPLE 3

Effectiveness on *Pratylenchus penetrans* with burdocks used as indicator

*Pratylenchus penetrans* cultured indoor with alfalfa callus were artificially inoculated into sterilized soil. The density of the nematodes was more than 1,000 per gr of soil. The nematode-inoculated soil was left in a room at 25° C. for 24 hours and then packed into unglazed pots in the same way as Test Example 2, followed by compound application. Then after 24 hours, the burdock seeds were sown therein (five seeds per pot). The carbam compound was applied in the same way as Test Example 2, and the burdock seeds were sown (5 seeds per pot) on the 10th day after the treatment. The test was performed in a glass hothouse (at a temperature of 25°–30° C.) and the degree of damage to roots and phytotoxicity were examined 50 days after the treatment. The results are shown in Table 3 below. The test was repeated three times. The degree of damage to the roots and pytotoxicity were expressed by the following rating.

TABLE 3

| Degree of damage to roots: | 0 | None |
|---|---|---|
| | 1 | Light |
| | 2 | Moderate |
| | 3 | Heavy |
| | 4 | Severe |
| Rate of phytotoxicity: | − | No sign of damage |
| | ± | Growth was slightly affected and leaf blades were discolored |
| | + | Growth was bad and leaf blades were discolored. |
| | ++ | Growth was very bad and all leaves were browned. |
| | +++ | Almost blasted |

| Compound | Dosage (kg/10a) | Degree of damage to roots | Rate of phyto-toxicity |
|---|---|---|---|
| Allyl-N,N-dimethyl-dithiocarbamate | 10 | 0 | − |
| | 5 | 0.1 | − |
| 50% wettable powder | 2.5 | 1.9 | − |
| 2-Methylallyl-N,N-dimethyldithiocarbamate | 10 | 0 | − |
| | 5 | 0 | − |
| 50% wettable powder | 2.5 | 1.7 | − |
| Propargyl-N,N-dimethyl-dithiocarbamate | 10 | 0 | − |
| | 5 | 0.7 | − |
| 50% wettable powder | 2.5 | 2.1 | − |
| Carbam | 10 | 0 | ± |
| 50% liquid | 5 | 0.89 | − |
| | 2.5 | 2.8 | − |
| Non-treated | − | 3.5 | − |

TEST EXAMPLE 4

Effectiveness on *Meloidogine incognita* in large-sized pots with tomatoes used as indicator plant The soil in which *Meloidogine incognita* were bred by using sweet potatoes as host plant was packed into the 1/2000 are pots (30 cm high) and a measured amount of compound granules prepared according to Example 5 were treated in the soil to the depth of 15 cm. The control of 20% DBCP (1,2-dibromo-3-chloropropane) granules were similarly applied. On the fifth day after the compound application, the tomato seedlings were transplanted in the pots (7 seedlings per pot). The test was conducted in a glass hothouse (25°–30° C.) and repeated twice. The rate of parasitic knots and phytotoxicity were examined 60 days after transplanting of the tomato seedlings. The results are shown in Table 4 below. The rate of parasitic knots and phytotoxicity were expressed by the following rating.

TABLE 4

| Rate of parasitic knots: | 0 | None |
|---|---|---|
| | 1 | Light |
| | 2 | Moderate |
| | 3 | Heavy |
| | 4 | Severe |
| Rate of pytotoxicity: | — | No sign of damage |
| | ± | Growth was slightly bad |
| | + | Growth was bad |
| | ++ | Growth was very bad |
| | +++ | Blasted |

| Compound | Dosage (kg/10a) | Rate of parasitic knots | Rate of phytotoxicity |
|---|---|---|---|
| Allyl-N,N-dimethyl-dithiocarbamate | 30 | 0 | ± |
| | 20 | 0 | — |
| 25% granules | 10 | 1 | — |
| DBCP | 30 | 0 | ± |
| 20% granules | 20 | 1 | — |
| | 10 | 1.5 | — |
| Non-treated | — | 3.5 | — |

TEST EXAMPLE 5

Nematocidal activity on *Bursaphelenchus lignicolus*

The tested nematodes were the groups of individuals, mostly larvae, of *Bursaphelenchus lignicolus* under indoor cultivation.

Each compound to be tested was dissolved in ethanol to 1% concentration and the solution was diluted to a desired concentration with Tween 80 (tradename for polyoxyethylene sorbitan monoolate manufactured by Kao Atras & Co., Ltd.). Each diluted solution was pipetted (10 ml) into a Syracuse watch glass, and the nematodes were placed in the respective watch glasses (150 to 200 nemadoes per glass) and bred at 27° C. for 48 hours. Thereafter, death and survival of the nematodes were examined microscopically to determine the mortality. The test was repeated three times. The results are shown in Table 5 below.

TABLE 5

| Compound | Mortality (%) | | |
|---|---|---|---|
| | 50$^{ppm}$ | 10$^{ppm}$ | 1$^{ppm}$ |
| Allyl-N,N-diethyldithio-carbamate | 100 | 83.5 | 25.9 |
| Allyl-N,N-dipropyldithio-carbamate | 100 | 75.1 | 25.9 |
| Crotyl-N,N-dimethyldithio-carbamate | 100 | 83.6 | 31.0 |
| DBCP (control) | 95.1 | 57.7 | 3.0 |

TEST EXAMPLE 6

Effectiveness on *Meloidogine incognita* with tomatoes used as indicator plant

The soil in which the nematodes (*Meloidogine incognita*) were bred by using sweet potatoes as host plant was packed into an unglazed pot having (5.5 cm-diameter and 5.5 cm-height), 50 gr of soil per pot, and a measured amount of a wettable powder prepared according to Example 7 was diluted with water and poured onto the surface of each pot. On the fifth day after said treatment, the tomato seeds were sown in the pots (10 seeds per pot). In the case of the carbam compound (control), a measured amount of said compound was absorbed into a piece of cotton and the cotton was placed in a 5 cm deep hole bored in the center of each pot and covered with soil, and on the 10th day after the treatment, tomato seeds were sown in the pots (10 seeds per pot). The test was conducted in a glass hothouse (at a temperature of 25°–30° C.), and the rate of parasitic knots and phytotoxicity were investigated one month after the treatment. The rate of parasitic knots and phytotoxicity were expressed by the following rating. The results were shown as in Table 6 below. The test was repeated three times.

TABLE 6

| Rate of parasitic knots: | 0 | None |
|---|---|---|
| | 1 | Light |
| | 2 | Moderate |
| | 3 | Heavy |
| | 4 | Severe |
| Rate of phytotoxicity: | — | No sign of damage |
| | ± | Slightly bad growth |
| | + | Bad growth |
| | ++ | Very bad growth' |
| | +++ | No germination or blasted |

| Compound | Dosage (kg/10a) | Rate of parasitic knots | Rate of phytotoxicity |
|---|---|---|---|
| Allyl-N,N-diethyldithio-carbamate | 10 | 0 | ± |
| | 5 | 0.5 | — |
| 50% wettable powder | 2.5 | 1.7 | — |
| Allyl-N,N-dipropyldithio-carbamate | 10 | 0 | ± |
| | 5 | 0.2 | — |
| 50% wettable powder | 2.5 | 1.2 | — |
| Crotyl-N,N-dimethyldithio-carbamate | 10 | 0 | — |
| | 5 | 0.1 | — |
| 50% wettable powder | 2.5 | 1.5 | — |
| (Control) | 10 | 0 | + |
| Carbam | 5 | 0.5 | ± |
| 50% liquid | 2.5 | 3.0 | — |
| Non-treated | — | 4 | — |

TEST EXAMPLE 7

Effectiveness on *Pratylenchus penetrans* with burdocks used as indicator plant

The nematodes (*Pratylenchus penetrans*) cultured indoor with alfalfa callus were inoculated artificially into sterilized soil. The density of nematodes was more than 1,000 per gr of soil. The thus inoculated soil was left in a room at 25° C. for 24 hours, then packed into the unglazed pots in the same way as Test Example 6 and treated with the test compounds. On 3rd day after the treatment, burdock seeds were sown in the pots (5 seeds per pot). In the case of the carbam compound (control), it was treated in the same way as Test Example 6 and the burdock seeds were sown in the pots (5 seeds per pot) on the 10th day after the treatment. The test was carried out in a glass hothouse (25°–30° C.), and the degree of damage to the roots and phytotoxicity were examined 50 days after the treatment. The results are shown in Table 7. The test was repeated three times. The degree of damage to the roots and phytotoxicity were expressed by the following rating.

TABLE 7

| Degree of damage to roots: | | |
|---|---|---|
| 0 | None | |
| 1 | Light | |
| 2 | Moderate | |
| 3 | Heavy | |
| 4 | Severe | |

Rate of phytotoxicity:

| | | |
|---|---|---|
| − | No sign of damage | |
| ± | Slightly bad growth | |
| + | Bad growth | |
| + | Very bad growth | |
| +++ | No germination or blasted | |

| Compound | Dosage (kg/10a) | Degree of damage to roots | Rate of phtotoxicity |
|---|---|---|---|
| Allyl-N,N-diethyldithio- | 10 | 0 | — |
| carbamate | 5 | 0.8 | — |
| 50% wettable powder | 2.5 | 1.8 | — |
| Allyl-N,N-dipropyldithio- | 10 | 0 | — |
| carbamate | 5 | 0.8 | — |
| 50% wettable powder | 2.5 | 2.0 | — |
| Crotyl-N,N-dimethyldithio- | 10 | 0 | — |
| carbamate | 5 | 0.5 | — |
| 50% wettable powder | 2.5 | 2.5 | — |
| (Control) | 10 | 0 | ± |
| Carbam | 5 | 0.6 | — |
| 50% liquid | 2.5 | 3.0 | — |
| Non-treated | — | 3.4 | — |

TEST EXAMPLE 8

Effectiveness on *Meloidogine incognita* in large-sized pots with tomatoes used as indicator plant The soil in which *Meloidogine incognita* were bred by using sweet potatoes as host plant was packed into the 1,2000 are pots (30 cm high), and a measured amount of test compound granules were treated in the soil to the depth of 15 cm. The control 20% DBCP (1,2-dibromo-3-chloropropane) granules were also similarly treated. On the fifth day after said treatment, tomato seedlings were transplanted in the pots (7 seedlings per pot). The test was conducted in a glass hothouse (25°–30° C.) and repeated twice, and on the 60th day after said transplanting, the rate of parasitic knots and phytotoxicity were examined. The rate of parasitic knots and phytotoxicity were expressed by the following rating. The results are shown in Table 8 below.

TABLE 8

| Rate of parasitic knots: | | |
|---|---|---|
| 0 | None | |
| 1 | Light | |
| 2 | Moderate | |
| 3 | Heavy | |
| 4 | Severe | |

Rate of phytototicity:

| | | |
|---|---|---|
| − | No sign of damage | |
| ± | Slight bad growth | |
| + | Bad growth | |
| ++ | Very bad growth | |
| +++ | Blasted | |

| Compound | Dosage (kg/10a) | Rate of parasitic knots | Rate of phyto-toxicity |
|---|---|---|---|
| Allyl-N,N-diethyldithio- | 30 | 0 | ± |
| carbamate | 20 | 0.5 | — |
| 25% granules | 10 | 1 | — |
| DBCP | 30 | 0.5 | ± |
| 20% granules | 20 | 1 | — |
| | 10 | 2 | — |

TABLE 8-continued

| Non treated | — | 4 | — |

As viewed above, the compounds according to this invention show an excellent effectiveness against the root-lesion nematodes and root-knot nematodes which damage seriously to the principal farm products, while said compounds are non-phytotoxic to burdocks and tomatoes.

What is claimed is:

1. A nematocidal composition containing as active ingredient(s) dithiocarbamate compound(s) represented by the general formula,

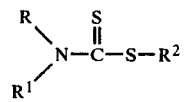

wherein R and R$^1$ are respectively a lower alkyl group, and R$^2$ is a group of —CH$_2$CH=CH$_2$,

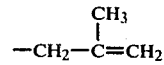

or

2. A nematocidal composition according to claim 1, wherein the lower alkyl group is a normal alkyl group having 1 to 3 carbon atoms.

3. A method for killing nematodes comprising treating soil infested with nematodes with a composition containing as active ingredients a dithiocarbamate compound represented by the general formula,

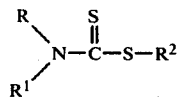

wherein R and R$^1$ are respectively a lower alkyl group, and R$^2$ is selected from the group consisting of —CH$_2$CH=CH$_2$,

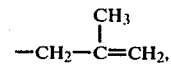

—CH$_2$C≡CH and —CH$_2$—CH=CHCH$_3$.

4. A method according to claim 3 where R and R$^1$ are both normal alkyl having 1 to 3 carbon atoms.

5. A method according to claim 3 wherein R$^2$ is —CH$_2$CH=CH$_2$,

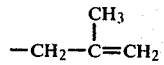

or —CH$_2$—CH=CHCH$_3$.

6. A method according to claim 5 wherein R$^2$ is —CH$_2$CH=CH$_2$.

7. A method according to claim 5 wherein R$^2$ is

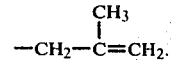

8. A method according to claim 5 wherein R$^2$ is —CH$_2$—CH=CHCH$_3$.

* * * * *